United States Patent [19]

Miller et al.

[11] Patent Number: 5,948,237
[45] Date of Patent: Sep. 7, 1999

[54] USE OF SARCOSINATES AS ASPHALTENE-DISPERSING AGENTS

[75] Inventors: Dennis Miller, Kelkheim; Axel Vollmer, Kriftel; Michael Feustel, Köngernheim; Peter Klug, Grossostheim, all of Germany

[73] Assignee: Clariant GmbH, Frankfurt, Germany

[21] Appl. No.: 08/949,722

[22] Filed: Oct. 14, 1997

[30] Foreign Application Priority Data

Oct. 15, 1996 [DE] Germany .................. 196 42 494

[51] Int. Cl.$^6$ .................................................. C10C 73/36
[52] U.S. Cl. ................. 208/22; 208/44; 585/950; 585/1; 524/64; 524/65
[58] Field of Search ................ 208/45, 48 AA, 208/309, 22; 585/950; 524/64, 65

[56] References Cited

U.S. PATENT DOCUMENTS

| | | | |
|---|---|---|---|
| 3,034,907 | 5/1962 | Kleeman et al. | 106/14 |
| 4,074,978 | 2/1978 | Panzer | 44/66 |
| 4,414,035 | 11/1983 | Newberry et al. | 134/3 |
| 4,455,149 | 6/1984 | Satake et al. | 44/51 |
| 4,614,236 | 9/1986 | Watkins et al. | 166/304 |
| 4,737,296 | 4/1988 | Watkins | 252/8.553 |
| 4,915,819 | 4/1990 | Chirnos | 208/309 |
| 4,929,341 | 5/1990 | Thirumalachar et al. | 208/309 |
| 4,931,164 | 6/1990 | Dickakian | 208/48 AA |
| 4,957,511 | 9/1990 | Ljusbeg-Wahren | 44/51 |
| 5,100,531 | 3/1992 | Stepheson | 208/22 |
| 5,421,993 | 6/1995 | Hille | 208/47 |
| 5,650,537 | 7/1997 | Beller et al. | 562/519 |
| 5,736,175 | 4/1998 | Cea | 426/6 |

FOREIGN PATENT DOCUMENTS

| | | |
|---|---|---|
| 2029465 | 5/1991 | Canada . |
| 2075749 | 2/1993 | Canada . |
| 0680948 | 11/1995 | European Pat. Off. . |
| 1212585 | 3/1960 | France . |
| 1214872 | 4/1960 | France . |
| 1545298 | 7/1969 | Germany . |
| 1545248 | 8/1969 | Germany . |
| 951138 | 3/1964 | United Kingdom . |
| 1085169 | 6/1966 | United Kingdom . |
| WO 88/07408 | 10/1988 | WIPO . |

OTHER PUBLICATIONS

J. Pet. Tecynol. 47 (1995) 782–787.
D.-L. Chang and H.S. fogler (SPE paper No. 25185, 1993).
Derwent Patent Family Report and/or Abstracts.
International Search Report.

*Primary Examiner*—Helane Myers
*Attorney, Agent, or Firm*—Miles B. Dearth

[57] ABSTRACT

The present invention relates to crude oils and products derived therefrom, comprising, as asphaltene-dispersing agent, sarcosinates of the formula (I)

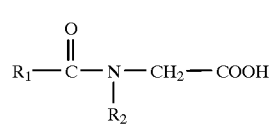

in which
$R_1$ is $C_7$–$C_{21}$-alkyl or -alkenyl and
$R_2$ is H or $C_1$–$C_{22}$-alkyl.

Precipitating out of asphaltenes is prevented by these dispersing agents.

6 Claims, No Drawings

USE OF SARCOSINATES AS ASPHALTENE-DISPERSING AGENTS

BACKGROUND OF THE INVENTION

Asphaltenes are constituents of crude oils. They comprise a large number of structures, in particular high molecular weight fused aromatic components with heteroatoms. In view of the complexity of their chemistry, asphaltenes are described as the oil fraction which is soluble in benzene but not in n-pentane.

In crude oil, asphaltenes are usually present as a colloidal dispersion. This is stabilized by oil resins.

Asphaltenes can precipitate out during production, refining, transportation and storage of crude oil and products derived therefrom, such as, for example, heavy heating oil or marine oil. Common causes of this precipitation are a reduction in the temperature or a change in the composition (for example evaporation of readily volatile constituents). Asphaltenes can also precipitate out on flowing through porous media. Flooding with $CO_2$ during the extraction process can make asphaltenes flocculate or precipitate out.

Some oils comprise hydrocarbon waxes which precipitate out at low temperatures. Interactions between the precipitating out of wax and asphaltenes can increase the total amount of substance precipitated out or the rate of formation thereof.

Asphaltenes which have precipitated out cause problems during production and during processing of crude oils. Asphaltenes are precipitated in valves, pipes and conveying devices. On hot surfaces, such as, for example, heat exchangers, carbonization of these precipitates can make their removal very difficult. The precipitates reduce the efficiency of plants and in the worst case can lead to a complete blockage and to a stop in production, which results in high costs.

Heavy oils, which are often used for powering ships, comprise considerable amounts of asphaltenes. Precipitating out of asphaltenes can lead both to poor combustion and to difficulties during handling and storage of the fuel. Combustion disturbances due to precipitating out of asphaltenes are also observed in power stations operated with heavy oils.

Bitumen, heavy oils and residues are sometimes diluted with solvents to reduce the viscosity for transportation. If asphaltenes precipitate out here, then there are problems during handling.

Precipitating out of asphaltenes can be prevented or reduced by small amounts of dispersing agents. These substances show one or more of the following effects:
a) the amount of precipitate is reduced;
b) the precipitate forms more slowly;
c) the precipitate is more finely divided; and
d) the tendency of the precipitate to be deposited on surfaces is reduced.

If precipitates of asphaltenes have already formed, they can be removed by using solvents. The addition of a dispersing agent can improve the effectiveness of these solvents.

A large number of asphaltene-dispersing agents are already known. CA 2 029 465 and CA 2 075 749 describe alkylphenol-formaldehyde resins in combination with hydrophilic-lipophilic vinyl polymers. The asphaltene-dispersing properties of dodecylbenzenesulfonic acid have been described in U.S. Pat. No. 4,414,035, and also by D. -L. Chang and H. S. Fogler (SPE paper No. 25185, 1993) and by M. N. Bouts et al. (J. pet. Technol. 47, 782–7, 1995). Oxalkylated amines are described in U.S. Pat. No. 5,421,993.

The dispersing agents known to date can only partly solve the problems caused by precipitating out of asphaltenes. Since oils vary in their composition, individual dispersing agents can operate effectively only in a limited range. Sometimes even small changes in the oil composition have a major effect on the dispersing properties for asphaltenes. In some cases, the known dispersing agents are therefore not satisfactory and additional types are necessary.

There was therefore the object of providing novel asphaltene-dispersing agents which do not have the disadvantages described for the dispersing agents known to date.

SUMMARY OF THE INVENTION

Surprisingly, it has been found that sarcosinates of the formula (I)

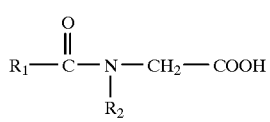

I can be used to prevent precipitating out and/or deposition of asphaltenes in crude oils and products derived therefrom.

The invention therefore relates to crude oils and products derived therefrom, comprising, as asphaltene-dispersing agent, sarcosinates of the formula (I)

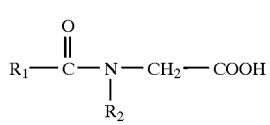

I in which
$R_1$ is $C_7$–$C_{21}$-alkyl or alkenyl, preferably $C_{11}$–$C_{17}$, and
$R_2$ is H or $C_1$–$C_{22}$-alkyl, preferably H, butyl or isobutyl.

DESCRIPTION OF THE PREFERRED EMBODIMENTS

The dispersing agents according to the invention are employed in a concentration of 1 to 10,000 ppm, preferably 2 to 2000 ppm.

For easier metering, these asphaltene-dispersing agents can be formulated as a solution in an oil-miscible solvent, such as, for example, aromatic hydrocarbons or mixtures of hydrocarbons and an aliphatic alcohol.

Effective asphaltene-dispersing agents are also obtained by combination of these sarcosinates with other components, in particular
a) alkylphenol-formaldehyde resins
b) oxalkylated amines,
c) alkylbenzenesulfonic acids,
d) wax-dispersing agents.

Dispersing agents which are based on a combination of substances may be less sensitive to a change in the composition of the oil; this improves their reliability.

EXAMPLES

Principle of the Dispersing Test

The dispersing, the precipitating out of asphaltenes depends on the nature of the hydrocarbon medium. Asphaltenes are soluble in aromatic but not in aliphatic hydrocarbons. Dispersing agents can thus be tested by dissolving the oil or extracted asphaltenes in an aromatic solvent and then adding an aliphatic hydrocarbon in order to produce a precipitate. Since asphaltenes are dark in color, the extent of the precipitate can be determined by a calorimetric measurement of the supernatant liquid. The darker the supernatant liquid, the more asphaltenes remain dispersed, i.e. the better the dispersing agent. This test is described in Canadian Patent 20 29 465. In our version of the test, the precipitating medium is chosen such that the asphaltenes precipitate out for the most part, but not completely.

Dispersing Test Procedure a) A 25% strength oil solution in toluene is filtered in order to remove impurities;
b) 9.5 ml of heptane, as a precipitating agent for asphaltenes, and 0.5 ml of toluene/dispersing agent mixture (25:1) are initially introduced into a graduated glass tube which holds a good 10 ml, and are shaken vigorously. This corresponds to a dispersing agent concentration of 2000 ppm. The amount of dispersing agent can be varied if required. Pure toluene is used for the blank samples;
c) 0.1 ml of the filtered oil solution is then added to the glass tube and the mixture is likewise shaken vigorously;
d) the entire system is left to stand for 2 hours without vibration. The asphaltenes which have precipitated out should be able to accumulate on the bottom of the tube;
e) after the end of this period, the volume of the sediment is estimated with the aid of the graduation, the appearance of the entire sample is recorded and then 1 ml of the supernatant phase is carefully removed with a pipette;
f) the quantity aspirated out is dissolved in 5 ml of toluene and measured photometrically at 600 nm.

Evaluation of the Dispersing Test

The following expression is taken as a relative measure of the dispersing action $$A = 100\ (D - D_0)/D_0,$$

in which $D$ and $D_0$ are the optical densities of the measurement solution and blank sample. The maximum value of $A$ which can be achieved, $A_{max}$, corresponds to complete dispersion of the asphaltenes. It can be estimated by carrying out a test without a dispersing agent and with toluene instead of heptane—the asphaltenes remain completely dispersed as a result.

The volume of the sediment provides further information on the effectiveness of the dispersing agent. The smaller the amount of sediment, the better the substance is dispersed.

Results

The investigations were carried out with a heavy oil which comprised considerable amounts of asphaltenes. Tables 1 and 2 show the results of the dispersing test with various substances according to the invention. Substances 2–6 were prepared by the method disclosed in EP-A-0 680 948.

TABLE 1

| | substances tested | | |
|---|---|---|---|
| Substance | | Chemistry | |
| No. | $R_1$ | $R_2$ | Description |
| 1 | $C_{17}H_{33}$ | H | Oleylsarcosine |
| 2 | i-$C_8H_{17}$ | n-$C_4H_9$ | Isononanoyl-n-butylglycine |
| 3 | $C_{15/17}H_{31/35}$ | i-$C_4H_9$ | Tallow fatty acid-iso-butylglycine |
| 4 | $C_{11/13}H_{23/27}$ | $C_{12/14}H_{25/29}$ | Cocoyl-cocoyl-glycine |
| 5 | $C_{11/13}H_{23/27}$ | n-$C_4H_9$ | Cocoyl-n-butylglycine |

TABLE 1-continued

| | substances tested | | |
|---|---|---|---|
| Substance | | Chemistry | |
| No. | $R_1$ | $R_2$ | Description |
| 6 | $C_{15/17}H_{31/35}$ | n-$C_4H_9$ | Tallow fatty acid-n-butylglycine |
| 7 | $C_{11/13}H_{23/27}$ | H | Lauroylsarcosine |

TABLE 2 tests results with 2000 ppm of dispersing agent

| | Dispersing effect | |
|---|---|---|
| Substance No. | A | Sediment (ml) |
| 1 | 334 | 0.3 |
| 2 | 238 | 0.6 |
| 3 | 270 | 0.5 |
| 4 | 323 | 0.3 |
| 5 | 241 | 0.5 |
| 6 | 247 | 0.6 |
| 7 | 290 | 0.4 |
| untreated | 0 | 1.0 |

Under these conditions, the maximum value for A, which corresponds to complete dispersion of the asphaltene, would be about 500.

It was possible to improve the dispersing properties of substance 1 by mixing nonylphenol-formaldehyde resin to this substance. A 1:1 mixture of these two substances thus showed an A value of 475.

We claim:

1. A crude oil or a product derived therefrom, comprising as asphaltene-dispersing agent a sarcosinate of the formula (I)

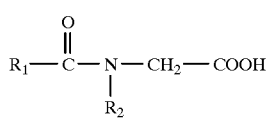

I in which
$R_1$ is $C_7$–$C_{21}$-alkyl or -alkenyl and
$R_2$ is H or $C_1$–$C_{22}$-alkyl.

2. A crude oil as claimed in claim 1, wherein
$R_1$ is $C_{11}$–$C_{17}$-alkyl or -alkenyl and
$R_2$ is H, butyl or isobutyl.

3. A process for dispersing asphaltenes in a crude oil or a product derived therefrom as claimed in claim 1, which comprises adding a sarcosinate in an amount of 1 to 10,000.

4. The process as claimed in claim 3, wherein an alkylphenol-formaldehyde resin, oxalkylated amine, wax-dispersing agent or any desired mixture thereof is additionally used.

5. A process for the dispersion of asphaltenes in a crude oil or a product derived therefrom, characterized in that sarcosinates as claimed in claim 1, in which $R_1$ is $C_7$–$C_{21}$ alkyl or -alkenyl and $R_2$ is H or $C_1$–$C_{22}$-alkyl, are added to said crude oil or product derived therefrom.

6. A process for dispersing asphaltenes in a crude oil or a product derived therefrom, comprising adding the sarcosinate as claimed in claim 1 to said crude oil or product derived therefrom in an amount of from 2 to 2000 ppm.

* * * * *